United States Patent [19]

Payne et al.

[11] Patent Number: 4,542,122

[45] Date of Patent: Sep. 17, 1985

[54] COBALT CATALYSTS FOR THE PREPARATION OF HYDROCARBONS FROM SYNTHESIS GAS AND FROM METHANOL

[75] Inventors: Virgil L. Payne; Charles H. Mauldin, both of Baton Rouge, La.

[73] Assignee: Exxon Research and Engineering Co., Florham Park, N.J.

[21] Appl. No.: 626,013

[22] Filed: Jun. 29, 1984

[51] Int. Cl.$^4$ .................... B01J 21/06; B01J 23/74; B01J 23/12
[52] U.S. Cl. .................... 502/325; 518/715
[58] Field of Search .................... 502/300, 325, 350; 518/715

[56] References Cited

U.S. PATENT DOCUMENTS

| | | | |
|---|---|---|---|
| 4,088,671 | 5/1978 | Kobylinski | 260/449 R |
| 4,338,089 | 7/1982 | Schaper et al. | 518/707 |
| 4,385,193 | 5/1983 | Bijwaard et al. | 585/310 |

FOREIGN PATENT DOCUMENTS 2073237 10/1981 United Kingdom .

OTHER PUBLICATIONS

92:129385h; The Synthesis of Solid Hydrocarbons from Methanol; Shima, Kensuke, Morita, Tauyoshi (Miyazaki Univ., Miyazaki, Japan); Nouveau Journal De-Chime, vol. 6, No. 10-1982, p. 459.
Fischer-Tropsch Synthesis of Hydrocarbons Over Ruthenium Supported on Transition Metal Oxides; Kikuchi, Nomura, Matsumoto and Morita (Waseda University, Tokyo, 160); Pan-Pacific Synfuels Conference, vol. I, Nov. 17-19, 1982, Tokyo, pp. 1-10.
Fischer-Tropsch Synthesis Over Titania-Supported Ruthenium Catalysts; Kikuchi, Matsumoto, Takahashi, Machino and Morita (Waseda University, 3-4-1 Okubo, Shinjuku, Tokyo, Japan); printed in the Netherlands; Applied Catalysis, 10 (1984), pp. 251-260.

*Primary Examiner*—W. J. Shine
*Attorney, Agent, or Firm*—Llewellyn A. Proctor

[57] ABSTRACT

A cobalt catalyst, especially a thoria promoted cobalt catalyst, formed by dispersing the cobalt, or cobalt and thoria, upon a titania or titania-containing support wherein the titania support is one having a rutile:anatase ratio of at least about 2:3. By passing methanol, or an admixture of carbon monoxide and hydrogen over the catalyst at reaction conditions, a distillate fuel constituted principally of an admixture of linear paraffin and olefins, particularly a $C_{10}+$ distillate can be formed. The distillate can be further refined and upgraded to high quality fuels, and other products such as mogas, diesel fuel, jet fuel, lubes and specialty solvents, particularly premium middle distillate fuels of carbon numbers ranging from about $C_{10}$ to about $C_{20}$.

17 Claims, No Drawings

COBALT CATALYSTS FOR THE PREPARATION OF HYDROCARBONS FROM SYNTHESIS GAS AND FROM METHANOL

BACKGROUND AND PROBLEMS i. Field of the Invention

This invention relates to catalyst compositions useful for the preparation of liquid hydrocarbons from synthesis gas, and from methanol. In particular, it relates to catalysts useful in a process wherein $C_{10}+$ distillate fuels, and other valuable products, are prepared by reaction of carbon monoxide and hydrogen, or methanol, over certain types of cobalt catalysts.

ii. The Prior Art

Methane is often available in large quantities from process streams either as an undesirable by-product in admixture with other gases, or as an off gas component of a process unit, or units. More importantly, however, methane is the principle component of natural gas, and it is produced in considerable quantities in oil and gas fields. The existence of large methane, natural gas reserves coupled with the need to produce premium grade transportation fuels, particularly middle distillate fuels, creates a large incentive for the development of a new gas-to-liquids process. The technology to convert coal or natural gas to synthesis gas is well established, and the conversion of the synthesis gas to hydrocarbons can be carried out via Fischer-Tropsch synthesis. On the other hand, the technology is also available to convert natural gas to methanol, a product of limited marketability. However, to utilize the existing technology, there is need for catalysts suitable for the conversion of methanol to high quality transportation fuels, particularly middle distillate fuels.

Fischer-Tropsch synthesis for the production of hydrocarbons from carbon monoxide and hydrogen is now well known in the technical and patent literature. The first commercial Fischer-Tropsch operation utilized a cobalt catalyst, though later more active iron catalysts were also commercialized. An important advance in Fischer-Tropsch catalysts occurred with the use of nickel-thoria on kieselguhr in the early thirties. This catalyst was followed within a year by the corresponding cobalt catalyst, 100 Co:18 ThO$_2$:100 kieselguhr, parts by weight, and over the next few years by catalysts constituted of 100 Co:18 ThO$_2$:200 kieselguhr and 100 Co:5 ThO$_2$:8 MgO:200 kieselguhr, respectively. The Group VIII non-noble metals, iron, cobalt, and nickel have been widely used in Fischer-Tropsch reactions, and these metals have been promoted with various other metals, and supported in various ways on various substrates. Most commercial experience has been based on cobalt and iron catalysts. The cobalt catalysts, however, are of generally low activity necessitating a multiple staged process, as well as low synthesis gas throughput. The iron catalysts, on the other hand, are not really suitable for natural gas conversion due to the high degree of water gas shift activity possessed by iron catalysts. Thus, more of the synthesis gas is converted to carbon dioxide in accordance with the equation: $H_2 + 2CO \rightarrow (CH_2)_x + CO_2$; with too litle of the synthesis gas being converted to hydrocarbons and water as in the more desirable reaction, represented by the equation: $2H_2 + CO \rightarrow (CH_2)_x + H_2O$.

There exists a need in the art for a catalyst useful for the conversion of methanol, and synthesis gas, respectively, at high conversion levels, and at high yields to premium grade transportation fuels, especially $C_{10}+$ distillate fuels; particularly without the production of excessive amounts of carbon dioxide.

OBJECTS

It is, accordingly, a primary objective of the present invention to supply these needs.

A particular object is to provide novel catalyst compositions useful for the conversion of methanol, and synthesis gas, i.e., carbon monoxide and hydrogen, to high quality distillate fuels characterized generally as admixtures of $C_{10}+$ linear paraffins and olefins.

THE INVENTION

These objects and others are achieved in accordance with the present invention embodying a cobalt catalyst, especially a thoria promoted cobalt catalyst, formed by dispersing the cobalt, or thoria and cobalt, upon a titania or titania-containing support wherein the rutile:anatase ratio of the support is at least about 2:3 to produce, by contact and reaction with methanol, or an admixture of carbon monoxide and hydrogen, at reaction conditions, a distillate fuel constituted principally of an admixture of linear paraffin and olefins, particularly a $C_{10}+$ distillate which can be further refined and upgraded to high quality fuels, and other products such as mogas, diesel fuel, jet fuel, lubes and specialty solvents, especially premium middle distillate fuels of carbon numbers ranging from about $C_{10}$ to about $C_{20}$.

The cobalt-titania catalyst, or thoria promoted cobalt-titania catalyst is one wherein cobalt, or cobalt and thoria, is composited, or dispersed upon titania, TiO$_2$, or a titania-containing carrier, or support, and the titania is one having a rutile:anatase weight ratio of at least about 2:3, as determined by ASTM D 3720-78: Standard Test Method for Ratio of Anatase to Rutile In Titanium Dioxide Pigments By Use of X-Ray Diffraction. A preferred, and more selective catalyst for use in methanol conversion reactions is one containing titania wherein the rutile:anatase ratio ranges from about 2:3 to about 3:2. In its preferred form the titania, or titania component of the carrier, or support, when used in the conversion of synthesis gas will contain a rutile:anatase ratio of at least about 3:2; generally from about 3:2 to about 100:1, or greater, and more preferably from about 4:1 to about 100:1, or greater. The cobalt, or cobalt and thoria, is dispersed on the support in catalytically effective amounts. In methanol conversion reactions the use of thoria with the cobalt is particularly preferred.

In terms of absolute concentration, suitably, the cobalt is dispersed on the support in amounts ranging from about 2 percent to about 25 percent, preferably from about 5 percent to about 15 percent, based on the total weight of the catalyst composition (dry basis). The thoria is dispersed on the support in amounts ranging from about 0.1 percent to about 10 percent, preferably from about 0.5 percent to about 5 percent, based on the total weight of the catalyst composition (dry basis). Suitably, the thoria promoted cobalt catalyst contains Co and ThO$_2$ in ratio of Co:ThO$_2$ ranging from about 20:1 to about 1:1, preferably from about 15:1 to about 2:1, based on the weight of the total amount of Co and ThO$_2$ contained on the catalyst. These catalyst compositions, it has been found, produce at reaction conditions a product which is predominately $C_{10}+$ linear paraffins and olefins, with very little oxygenates. These catalysts provide high selectivity, high activity and good activity maintenance in methanol conversion reactions, or in the conversion of carbon monoxide and hydrogen to distillate fuels.

In conducting methanol conversion reactions the partial pressure of methanol within the reaction mixture is generally maintained above about 100 pounds per square inch absolute (psia), and preferably above about 200 psia. It is preferable to add hydrogen with the methanol. Suitably methanol, and hydrogen, are employed in molar ratio of $CH_3OH:H_2$ above about 4:1 and preferably above 8:1, to increase the concentration of $C_{10}+$ hydrocarbons in the product. Suitably, the $CH_3OH:H_2$ molar ratio, where hydrogen is employed, ranges from about 4:1 to about 60:1, and preferably the methanol and hydrogen are employed in molar ratio ranging from about 8:1 to about 30:1. Inlet hydrogen partial pressures preferably range below about 80 psia, and more preferably below about 40 psia; inlet hydrogen partial pressures preferably ranging from about 5 psia to about 80 psia, and more preferably from about 10 psia to about 40 psia. In general, the reaction is carried out at liquid hourly space velocities ranging from about $0.1\ hr^{-1}$ to about $10\ hr^{-1}$, preferably from about $0.2\ hr^{-1}$ to about $2\ hr^{-1}$, and at temperatures ranging from about 150° C. to about 350° C., preferably from about 180° C. to about 250° C. Methanol partial pressures preferably range from about 100 psia to about 1000 psia, more preferably from about 200 psia to about 700 psia. The product generally and preferably contains 60 percent, or greater, and more preferably 75 percent, or greater, $C_{10}+$ liquid hydrocarbons which boil above 160° C. (320° F.).

In conducting synthesis gas reactions the total pressure upon the reaction mixture is generally maintained above about 80 psig, and preferably above about 140 psig, and it is generally desirable to employ carbon monoxide, and hydrogen, in molar ratio of $H_2:CO$ above about 0.5:1 and preferably equal to or above 2:1 to increase the concentration of $C_{10}+$ hydrocarbons in the product. Suitably, the $H_2:CO$ molar ratio ranges from about 0.5:1 to about 4:1, and preferably the carbon monoxide and hydrogen are employed in molar ratio $H_2:CO$ ranging from about 2:1 to about 3:1. In general, the reaction is carried out at gas hourly space velocities ranging from about 100 V/Hr/V to about 5000 V/Hr/V, preferably from about 300 V/Hr/V to about 1500 V/Hr/V, and at temperatures ranging from about 160° C. to about 290° C., preferably from about 190° C. to about 260° C. Pressures preferably range from about 80 psig to about 600 psig, more preferably from about 140 psig to about 400 psig. The product generally and preferably contains 60 percent, or greater, and more preferably 75 percent, or greater, $C_{10}+$ liquid hydrocarbons which boil above 160° C. (320° F.).

Cobalt-titania, and thoria promoted cobalt-titania catalysts exhibit high activity and selectivity in the conversion of methanol, or conversion of carbon monoxide and hydrogen to $C_{10}+$ distillate fuels. The catalysts employed in the practice of this invention are prepared by techniques known in the art for the preparation of these and other catalysts. The catalyst can, e.g., be prepared by gellation, or cogellation techniques. Suitably, however, cobalt can be composited alone, or with the thoria, upon a previously pilled, pelleted, beaded, extruded, or sieved titania or titania-containing support material by the impregnation method. In preparing catalysts, the metal, or metals, is deposited from solution on the support to provide the desired absolute amount of the metal, or metals. Suitably, the cobalt is composited with the support by contacting the support with a solution of a cobalt-containing compound, or salt, e.g., a nitrate, carbonate or the like. The thoria, where thoria is to be added, can then be composited with the support in similar manner, or the thoria can first be impregnated upon the support, followed by impregnation of the cobalt. Optionally, the thoria and cobalt can be coimpregnated upon the support. The cobalt compounds used in the impregnation can be any organometallic or inorganic compound which decomposes to give cobalt oxide upon calcination, such as cobalt nitrate, acetate, acetylacetonate, naphthenate, carbonyl, or the like. Cobalt nitrate is especially preferred while cobalt halide and sulfate salts should generally be avoided. The salts may be dissolved in a suitable solvent, e.g., water, or hydrocarbon solvent such as acetone, pentane or the like. The amount of impregnation solution used should be sufficient to completely immerse the carrier, usually within the range from about 1 to 20 times the carrier by volume, depending on the concentration of the cobalt-containing compound in the impregnation solution. The impregnation treatment can be carried out under a wide range of conditions including ambient or elevated temperatures. Metal components other than thorium may also be added as promoters. Exemplary of such promoters are nickel, platinum, palladium, rhodium and lanthanium. In general, however, the addition of these metals have not been found to provide any significant benefit. In fact, surprisingly, the addition of copper and iron appear to have had a somewhat adverse effect upon the reaction. For this reason, the preferred catalyst is one which consists essentially of cobalt, or cobalt and thoria, dispersed upon the titania, or titania-containing support; or, in other words, catalysts which do not contain a significant amount of a metal, or metals, other than cobalt, or metals other than cobalt and thorium, dispersed upon the titania or titania-containing support.

Titania is used as a support, or in combination with other materials for forming a support. The titania used for the support however, is necessarily one which contains a rutile:anatase ratio of at least about 2:3, as determined by x-ray diffraction (ASTM D 3720-78). The titania supports used in the production of methanol catalysts contain a rutile:anatase ratio of preferably from about 2:3 to about 3:2. Preferably in conducting synthesis gas conversion reactions, the rutile:anatase ratio is at least about 3:2. Preferably, when the catalyst is used in synthesis gas conversion reactions, the titania contains a rutile:anatase ratio of from about 3:2 percent to about 100:1, or greater, preferably from about 4:1 to about 100:1, or greater. The surface area of such forms of titania are less than about 50 $m^2/g$. These weight concentrations of rutile provide generally optimum activity, and $C_{10}+$ hydrocarbon selectivity without significant gas and $CO_2$ make.

The catalyst, after impregnation, is dried by heating at a temperature above about 0° C., preferably between 0° C. and 125° C., in the presence of nitrogen or oxygen, or both, in an air stream or under vacuum. It is necessary to activate the cobalt-titania, or thoria promoted cobalt-titania catalyst prior to use. Preferably, the catalyst is contacted with oxygen, air, or other oxygen-containing gas at temperature sufficient to oxidize the cobalt and convert the cobalt to $Co_3O_4$. Temperatures ranging above about 150° C., and preferably above about 200° C. are satisfactory to convert the cobalt to the oxide, but temperatures above about 500° C. are to be avoided unless necessary for regeneration of a severely deactivated catalyst. Suitably, the oxidation of the cobalt is achieved at temperatures ranging from about 150° C. to about 300° C. The metal, or metals, contained on the catalyst are then reduced. Reduction is performed by contact of the catalyst, whether or not previously oxidized, with a reducing gas, suitably with hydrogen or a hydrogen-containing gas stream at temperatures above about 200° C.; preferably above about 250° C. Suitably, the catalyst is reduced at temperatures ranging from about 200° C. to about 500° C. for periods ranging from about 0.5 to about 24 hours at pressures ranging from ambient to about 40 atmospheres. A gas containing hydrogen and inert components in admixture is satisfactory for use in carrying out the reduction.

The cobalt, and thoria promoted cobalt-titania catalysts of this invention can be regenerated, and reactivated to restore their initial activity and selectivity after use by stripping the catalyst with a hydrocarbon solvent, or with a gas. Preferably the catalyst is stripped with a gas, most preferably with hydrogen, or a gas which is inert or non-reactive at stripping conditions such as nitrogen, carbon dioxide, or methane. The stripping removes the hydrocarbons which are liquid at reaction conditions. Gas stripping can be performed at substantially the same temperatures and pressures at which the reaction is carried out. Pressures can be lower however, as low as atmospheric. Temperatures can thus range from about 160° C. to about 290° C., preferably from about 190° C. to about 260° C., and pressures from about atmospheric to about 600 psig, preferably from about 140 psig to about 400 psig.

If it is necessary to remove coke from the catalyst, the catalyst can be contacted with a dilute oxygen-containing gas and the coke burned from the catalyst at controlled temperature below the sintering temperature of the catalyst. The temperature of the burn is controlled by controlling the oxygen concentration and inlet gas temperature, this taking into consideration the amount of coke to be removed and the time desired to complete the burn. Generally, the catalyst is treated with a gas having an oxygen partial pressure of at least about 0.1 psi, and preferably in the range of from about 0.3 psi to about 2.0 psi to provide a temperature ranging from about 300° C. to about 550° C., at static or dynamic conditions, preferably the latter, for a time sufficient to remove the coke deposits. Coke burn-off can be accomplished by first introducing only enough oxygen to initiate the burn while maintaining a temperature on the low side of this range, and gradually increasing the temperature as the flame front is advanced by additional oxygen injection until the temperature has reached optimum. Most of the coke can be readily removed in this way. The catalyst is then reactivated, reduced, and made ready for use by treatment with hydrogen or hydrogen-containing gas as with a fresh catalyst.

The invention will be more fully understood by reference to the following examples and demonstrations which present comparative data illustrating its more salient features.

The data given in the examples which follow were obtained in a small fixed bed reactor unit, gas chromatographic analytical data having been obtained during the runs which were conducted over various periods. All parts are in terms of weight units except as otherwise specified. Feed compositions are expressed as molar ratios of the components.

The "Schulz-Flory Alpha" is a known method for describing the product distribution in Fischer-Tropsch synthesis reactions. The Schulz-Flory Alpha is the ratio of the rate of chain propagation to the rate of propagation plus termination, and is described from the plot of ln (Wn/n) versus n, where Wn is the weight fraction of product with a carbon number of n. In the examples below, an Alpha value was derived from the $C_{10}/C_{20}$ portion of the product. The Alpha value is thus indicative of the selectivity of the catalyst for producing heavy hydrocarbons from the synthesis gas, and is indicative of the approximate amount of $C_{10}+$ hydrocarbons in the product. For example, a Schulz-Flory Alpha of 0.80 corresponds to about 35% by weight of $C_{10}+$ hydrocarbons in the product, a generally acceptable level of $C_{10}+$ hydrocarbons. A Schulz-Flory Alpha of 0.85, a preferred Alpha value, corresponds to about 54% by weight of $C_{10}+$ hydrocarbons in the products, and a Schulz-Flory Alpha of 0.90, a more preferred Alpha value, corresponds to about 74% by weight of $C_{10}+$ hydrocarbons in the product.

The catalysts of this invention used in the examples below were prepared by the following procedure: Titania (Degussa P-25 $TiO_2$) was used as the support for all of the catalysts after mixing with sterotex, and after pilling, grinding, and screening to either 60–150 mesh or 16–20 mesh (Tyler). Two versions of $TiO_2$ were prepared by calcining portions of the $TiO_2$ in air at 500° C. and 600° C., respectively, overnight. This gave $TiO_2$ supports with the following properties:

| Calcination Temperature, °C. | Rutile:Antase Ratio[1] | Surface Area $m^2/g$ | Pore Volume ml/g |
|---|---|---|---|
| 500 | 1.2:1 | 33–36 | 0.18–0.40 |
| 600 | >30:1 | 10–16 | 0.11–0.15 |

Catalysts, of 16–20 mesh size, were prepared from selected portions of these materials by simple impregnation of the support with cobaltous nitrate or perrhenic acid, or both, from acetone solution using a rotary evaporator, drying in a vacuum oven at 150° C., and calcining of the catalysts for three hours in flowing air in a quartz tube. The catalysts were charged to a reactor, reduced in $H_2$ at 450° C. for one hour, and then reacted with syngas or methanol at the conditions described in the examples.

EXAMPLES

A. Methanol Conversion

Examples 1 through 6 which follow exemplify methanol conversion reactions.

In the example which immediately follows a series of runs were conducted with a thoria promoted cobalt-titania catalyst to demonstrate the effect of pressure, notably methanol partial pressure in converting methanol, and hydrogen, to hydrocarbons.

Example 1

A feed constituting an admixture of methanol and hydrogen in varying molar ratios of $CH_3OH:H_2$ was contacted over a thoria promoted cobalt-titania catalyst (12% Co-2% $ThO_2$-$TiO_2$) at total pressures ranging from ambient to 600 pounds per square inch gauge, psig, methanol partial pressures ranging from 2 to 492 psia, at a temperature of 230° C. and at space velocities of 3500 GHSV and 500 GHSV, respectively. The feed was diluted in certain cases with carbon dioxide and argon (Ar); the argon being added to maintain good operability in terms of obtaining accetable material balances. Reference is made to Table I.

TABLE I

12% Co-2% ThO$_2$—TiO$_2$

| Pressure | | | | | | |
|---|---|---|---|---|---|---|
| Total, psig | 0 | 40 | 100 | 250 | 400 | 600 |
| CH$_3$OH partial, psia | 2 | 44 | 92 | 212 | 332 | 492 |
| Temperature, °C. | | | 230 | | | |
| Feed Composition | 1 CH$_3$OH: 40 CH$_3$OH:2 H$_2$:1 CO$_2$:7 Ar 5.7 H$_2$ | | | | | |
| GHSV, Hr.$^{-1}$ | 3500 | | | 500 | | |
| CH$_3$OH Conversion | 11 | 44 | 46 | 53 | 70 | 76 |
| Conversion rate g/hr/g × 10$^2$ | 8 | 23 | 24 | 28 | 37 | 40 |
| Carbon Product Distribution, Wt % | | | | | | |
| CO | 91.9 | 79.3 | 47.6 | 11.6 | 3.1 | 0.6 |
| CO$_2$ | 0.4 | 0.3 | 3.6 | 10.4 | 17.0 | 20.9 |
| CH$_4$ | 7.7 | 9.4 | 9.5 | 7.9 | 8.6 | 11.5 |
| C$_2$+ | — | 11.1 | 44.3 | 70.1 | 71.3 | 67.0 |

Inlet methanol partial pressures ranging above about 100 psia, and preferably above about 200 psia, it has been found are required to ensure optimum conversion of methanol to hydrocarbons. Low inlet methanol partial pressures favor conversion of methanol to only H$_2$ and CO with very little hydrocarbon production. The impact of pressure on conversion and selectivity are clearly illustrated in Table I. Inlet methanol partial pressures should range from about 100 psia to about 1000 psia, preferably from about 200 psia to about 700 psia. Total pressure will depend on the amount of H$_2$, CO$_2$, or other inerts present in the reaction mixture.

Low partial pressures of hydrogen are preferred in order to maximize the yield of the desired heavy hydrocarbons at the expense of light hydrocarbons. For cobalt-titania, and thoria promoted cobalt-titania catalysts, the preferred inlet hydrogen partial pressure is generally maintained below about 80 psia, and preferably below about 40 psia.

Example 2

Example 1 was repeated utilizing both cobalt-thoria-titania catalyst, and an unpromoted cobalt-titania catalyst, at 400 psig, GHSV=500, 40 CH$_3$OH:2 H$_2$:1 CO$_2$:7 Ar. Reference is made to Table II. As shown in the table, the selectivity to heavy hydrocarbons is particularly high, especially at low temperature.

TABLE II 400 psig, GHSV = 500, 40 CH$_3$OH:2 H$_2$:1 CO$_2$7 Ar

| Catalyst | 12% Co-2% ThO$_2$—TiO$_2$ | | 12% Co—TiO$_2$ |
|---|---|---|---|
| Temperature, °C. | 200 | 230 | 230 |
| CH$_3$OH Conversion, 35 hr | 30 | 70 | 52 |
| Carbon Product Distribution, Wt. % | | | |
| CO | 2.8 | 3.1 | 5.5 |
| CO$_2$ | 7.2 | 17.0 | 12.9 |
| Dimethyl ether | 0.4 | 0.3 | 0.2 |
| CH$_4$ | 4.2 | 8.6 | 11.2 |
| C$_2$+ | 85.4 | 71.0 | 70.2 |
| Wt. % CH$_4$ in hydrocarbon | 4.7 | 10.8 | 13.8 |
| Schulz-Flory Alpha | 0.92 | 0.88 | 0.86 |

From the values given for the Schulz-Flory Alpha, it is apparent that the conversion of the methanol to heavy hydrocarbons, and the selectivity of the catalysts for producing C$_{10}$+ hydrocarbons are quite high. The Co-TiO$_2$ catalyst produces about 58% by weight C$_{10}$+ hydrocarbons in the product, and the ThO$_2$ promoted Co-TiO$_2$ catalyst produces a product containing approximately 65% by weight and 80% by weight C$_{10}$+ hydrocarbons, at 230° C. and 200° C., respectively.

Example 3

The product made from the Co-ThO$_2$-TiO$_2$ catalysts consists predominately of linear olefins and paraffins with a small amount of branched paraffins and olefins. Reference is made to Table III which shows the distribution of compounds within the C$_8$ fraction obtained by reaction of the methanol, and hydrogen, over the (12% Co-1% ThO$_2$-TiO$_2$), after 35 hours, at 230° C., 400 psig, GHSV=500 and 40 CH$_3$OH:2 H$_2$:1 CO$_2$:7 Ar.

TABLE III

| Component in C$_8$ | Wt. % |
|---|---|
| n-octane | 78.2 |
| 1-octene | 0.6 |
| 4-octenes | 6.5 |
| 2-methylheptane | 4.8 |
| 3-methylheptane | 6.9 |
| 4-methylheptane | 3.0 |

Hydrogen in relatively small amount, as earlier suggested, is desirable to promote conversion of the methanol to hydrocarbons. The absolute hydrogen concentration is also of importance in promoting conversion, selectivity and yield in the production of the C$_{10}$+ hydrocarbons from methanol. Partial pressures less than about 80 psia are preferred, and more preferably less than 40 psia, in order to produce the higher molecular weight liquid hydrocarbons. H$_2$ partial pressures above about 80 psia, or even 40 psia, favor a lighter, more paraffinic product.

Example 4

An admixture constituted of methanol and argon to which hydrogen was added in varying concentrations was passed into a reactor charged with a thoria promoted cobalt-titania catalyst, at 230° C., CH$_3$OH=332 psia, argon (83-H$_2$ psia) and GHSV=500. Measurements were made of the CH$_3$OH conversion, and carbon product distribution in terms of weight percent hydrocarbons, carbon monoxide, carbon dioxide and dimethyl ether (DME) formation. The results are given in Table IV.

TABLE IV

230° C., CH$_3$OH = 332 psia, Argon (83-H$_2$ psia), GHSV = 500

| Inlet H$_2$Partial Pressure psia | 0 | 17 | 83 |
|---|---|---|---|
| CH$_3$OH Conversion, Wt. % | 38 | 52 | 83 |
| Carbon Product Distribution, Wt. % | | | |
| CO | 8.5 | 3.9 | 0.9 |
| CO$_2$ | 11.3 | 8.9 | 12.2 |
| DME | 1.0 | 0.4 | 0.1 |
| CH$_4$ | 4.6 | 5.7 | 15.9 |
| C$_2$+ | 74.6 | 81.1 | 70.9 |
| Wt. % CH$_4$ in Hydrocarbon | 5.8 | 6.6 | 18.3 |

The addition of hydrogen to the reactor, it will be observed, increases the amount of methanol conversion. A hydrogen inlet pressure of 17 psia thus raises the conversion of the methanol by 14 percent (52%-38%), and the conversion of C$_2$+ hydrocarbons is increased by 6.5 percent (81.1%-74.6%). Increasing the inlet hydrogen partial pressure to 83 psia raises the amount of methanol conversion an additional 31 percent, viz., from 52 wt. % to 83 wt. %. However, C$_2$+ hydrocarbon selectivity is decreased somewhat, i.e., from 81.1 wt. % to 70.9 wt. %. Moreover, the hydrocarbon product is somewhat lighter, as indicated by the higher methane, and a Schulz-Flory Alpha of 0.82 is obtained.

Example 5

A series of runs were made, at similar conditions, by contact of methanol with fixed beds of catalyst, as identified in Table V, contained in a stainless steel tube reactor. The runs were conducted at 230° C., 400 psig, GHSV= 500 and 40 $CH_3OH$:2 $H_2$:1 $CO_2$:7 Ar. Measurements were made of the $CH_3OH$ conversion with each of these catalysts, and analysis made of the wt. % carbon product distribution in terms of CO, $CO_2$, dimethyl ether, $CH_4$ and $C_2+$ hydrocarbons. The wt. % methane that was produced was also recorded. Reference is made to Table V.

TABLE V

230° C., 400 psig, GHSV = 500, 40 $CH_3OH$:2 $H_2$:1 $CO_2$:7 Ar

| Catalyst | $CH_3OH$ Conversion | Carbon Product Distribution, Wt. % | | | | | Wt. % $CH_4$ in Hydrocarbons |
|---|---|---|---|---|---|---|---|
| | | CO | $CO_2$ | DME | $CH_4$ | $C_2+$ | |
| 12% Co-2% $ThO_2$—$TiO_2$ | 70 | 2.9 | 12.6 | 0.5 | 7.4 | 76.6 | 8.8 |
| 100 Co:5 $ThO_2$: 8 MgO:200 Kieselguhr[1] | 97 | 1.0 | 38.4 | — | 19.5 | 41.1 | 32.2 |
| 9 Co:1 Cu:2 ThOhd 2[2] | 20 | 16.7 | 42.4 | 0.2 | 5.2 | 35.5 | 12.8 |
| 12% Co—$SiO_2$ | 38 | 4.3 | 22.3 | 0.1 | 7.0 | 66.3 | 9.6 |
| 12% Co—$Al_2O_3$ | 64 | 2.8 | 21.8 | 2.4 | 9.9 | 63.1 | 13.6 |

[1]Prepared by procedure given at page 137 and following; The Fischer-Tropsch and Related Syntheses, Storch, Golumbic and Anderson, John Wiley and Sons, Inc., New York (1951).
[2]Shima, K.; Morita, T.; Mujazoki Diagaku Kogakuba Kenkyu, 25, 19–24 (1979).

These data show that the thoria promoted cobalt-titania catalyst, as contrasted with prior art cobalt catalysts, is clearly the superior catalyst. It produces high conversion of the methanol (70 wt. %), and high production of $C_2+$ hydrocarbons (76.6 wt. %) with low methane in the carbon product distribution (8.8 wt. %). Whereas the 100 Co:5 $ThO_2$:8 MgO:200 Kieselguhr catalyst provides extremely high conversion of the methanol (97 wt. %), the production of $C_2+$ hydrocarbons (41.1 wt. %) is extremely low, and the production of $CO_2$ is unacceptably high (38.4 wt. %). Essentially one-third (32.2 wt. %) of the total hydrocarbons that are produced is methane. The methanol conversion level (20 wt. %) of the 9 Co:1 Cu:2 $ThO_2$, albeit a thoria promoted cobalt catalyst, is abysmal; and the $CO_2$ production level (42.4 wt. %) unacceptable. Only 35.5 wt. % of the carbon product distribution is hydrocarbons. The methanol conversion level of the 12% Co-$SiO_2$ (38 wt. %) is likewise poor, with fairly high production of $CO_2$ (22.3 wt. %). The 12% Co-$Al_2O_3$ catalyst, while superior to the 9 Co:1 Cu:2 $ThO_2$ and 12% Co-Si-$O_2$ catalysts, provides only 64 wt. % conversion of the methanol, with high production of $CO_2$ (21.8 wt. %). The $C_2+$ hydrocarbons product make is only 63.1 wt. % as compared with 76.6 wt. % for the 12% Co-2% $ThO_2$-$TiO_2$ catalyst.

Example 6

The following data show the effect of different rutile contents on cobalt-titania catalysts used in the conversion of methanol to hydrocarbons. Thus, two 12% Co-$TiO_2$ catalysts, identical except that the $TiO_2$ base used to form one catalyst had a rutile:anatase weight ratio of 1.2:1, and the other a rutile:anatase weight ratio greater than 30:1, were used to convert methanol to hydrocarbons. The runs, made at identical conditions, were made at 230° C., 400 psig, GHSV = 500 and 40 $CH_3OH$:2 $H_2$:1 $CO_2$:7 Ar. Reference is made to Table VI.

TABLE VI

Effect of Rutile Content on 12% Co-$TiO_2$ Catalysts
230° C., 400 psig, GHSV = 500, 40 $CH_3OH$:2 $H_2$:1 $Co_2$:7 AR

| $TiO_2$ Properties | | |
|---|---|---|
| Rutile:Anatase Ratio, Wt. | 1.2:1 | >30:1 |
| Surface Area, $m^2$/g | 36 | 10 |
| Pore Volume, ml/g | 0.30 | 0.11 |
| $CH_3OH$ Conversion | 66 | 100 |
| Carbon Product Distribution, Wt. % | | |
| CO | 2.6 | 0.8 |
| $CO_2$ | 15.6 | 27.8 |
| $CH_4$ | 9.0 | 17.1 |
| $C_2+$ | 72.8 | 54.3 |

These data clearly show that the catalyst which contains 1.2:1 ratio of rutile:anatase is the superior catalyst. Albeit the catalyst which contains a weight ratio of >30:1 rutile:anatase provides higher conversion, the methane gas make is almost double that of the other catalyst (17.1% vs. 9.0%), and the catalyst is far less selective in the production of $C_2+$ hydrocarbons (54.3% vs. 72.8%). Moreover, the catalyst which contains >30:1 rutile:anatase is more active in converting the methanol to carbon dioxide (27.8% vs. 15.6%).

B. Synthesis Gas Conversion

Examples 7 through 9 which follow exemplify synthesis gas conversion.

In the example which immediately follows a series of runs were conducted with several known Fischer-Tropsch catalysts, these being compared with a run using a cobalt-titania catalyst to demonstrate the particularly high effectiveness of the latter in converting synthesis gas to hydrocarbons.

Example 7

A feed constituted of an admixture of carbon monoxide and hydrogen in molar ratio of $H_2$:CO of 2:1 was contacted over a cobalt-titania catalyst (Catalyst A; 12% Co-$TiO_2$; 0.9:1 rutile:anatase) and several known cobalt catalysts, viz., 100 Co:5 $ThO_2$:8 MgO:200 kieselguhr (Catalyst B), 12% Co/$SiO_2$ (Catalyst C) and 25 Co:1.8 Ti:100 $SiO_2$ (Catalyst D; U.S. Pat. No. 4,358,193), respectively, at temperature of 230° C., at a pressure of 150 psig, and at a space velocity of 400 $hr^{-1}$. The data shown in Table VII demonstrate the level of CO conversion 70 hours after initiation of the runs, the $CO_2$ selectivity, $CH_4$ selectivity, $C_2+$ selectivity, and the Shulz-Flory Alpha value, which is a measure of the ability of a catalyst to produce $C_{10}+$ hydrocarbons.

TABLE VII

Selectivity of Various Co Catalysts
T = 230° C., P = 150 psig, GHSV = 400 hr$^{-1}$ H$_2$:CO = 2

|  | CO Conversion @ 70 Hours | $CO_2$ Select. Wt. % | $CH_4$ Select. Wt. % | $C_2+$ Select. Wt. % | Shulz-Flory Alpha |
|---|---|---|---|---|---|
| Catalyst A 12% Co/TiO$_2$ | 88 | 1.1 | 8.6 | 90.3 | 0.91 |
| Catalyst B 100 Co:5 ThO$_2$: 8 MgO:200 KG[1] | 43 | 4.3 | 10.3 | 86.4 | — |
| Catalyst C 12% Co/SiO$_2$ | 72 | 1.6 | 8.7 | 89.7 | 0.85 |
| Catalyst D 25 Co:1.8 Ti: 100 SiO$_2$ | 21 | 1.9 | 13.8 | 84.3 | 0.74 |

[1]Prepared by procedure given at Page 137 and following; The Fischer-Tropsch and Related Syntheses, Storch, Golumbic and Anderson, John Wiley and Sons, Inc., New York (1951).

These data thus clearly show that Catalyst A, the Co/TiO$_2$ catalyst, is unique as regards its superior activity and selectivity. Moreover, the high Shulz-Flory Alpha value indicates an ability of this catalyst to produce in the product more than about 75% $C_{10}+$ hydrocarbons.

The following data show that the rutile content of the TiO$_2$ support from which the catalyst is formed is significant, the CO conversion of the catalyst increasing as the rutile content of the TiO$_2$ support is increased.

The following example demonstrates the effect of the rutile content of the TiO$_2$ supports from which cobalt-titania catalysts are formed, and the effects of the cobalt metal distribution upon the surface of the supports. In a first pair of runs, the rutile content of one support from which a catalyst is formed has a rutile:anatase ratio of 1.2:1, and the other a rutile:anatase ratio >30:1. In a second pair of runs, the rutile:anatase ratio of one support from which a catalyst is formed is about 1.2:1, and the other >30:1.

Example 8

Two 12% Co/TiO$_2$ catalysts were formed for use in a first pair of side-by-side runs by impregnating cobalt upon two portions of TiO$_2$ 16-20 mesh (Tyler) particles, the first portion having a rutile:anatase ratio of about 1.2:1 and the other a rutile:anatase of >30:1. Reference is made to Table VIII, Columns 2 and 3. Two additional portions of a 16-20 mesh (Tyler) TiO$_2$ were similarly impregnated with cobalt, the first having a rutile:anatase ratio of about 1.2:1 and the other a rutile:anatase ratio of >30:1. Reference is made to Table VIII, Columns 4 and 5. The first pair of catalysts (Columns 2 and 3) were similarly dried, and then calcined in air for 3 hours at 250° C. The second pair of catalysts (Columns 4 and 5) were then similarly dried and then calcined in air for 3 hours at 500° C. These catalysts were then charged in equal quantities to the fixed bed reactor as previously described, reduced with hydrogen, and separate runs made with each catalyst at identical conditions, viz., 200° C., 280 psig, GHSV = 1000 and H$_2$:CO of 2.15:1. The following data was taken after 20 hours operation, reference again being made to Table VIII.

TABLE VIII

Effect of Rutile Content, and Cobalt Metal Dispersion, on 12% Co/TiO$_2$ Catalyst
16-20 Mesh, 200° C., 280 psig, GHSV = 1000 H$_2$/CO = 2.15

| TiO$_2$ Properties | | | | |
|---|---|---|---|---|
| Rutile:Anatase Ratio, Wt. | 1.2:1 | >30:1 | 1.2:1 | >30:1 |
| Surface Area M$^2$/g | 36 | 10 | 33 | 10 |
| Pore Volume ml/g | 0.30 | 0.11 | 0.28 | 0.11 |
| Air Treat, °C. (3 Hrs.) | 250 | 250 | 500 | 500 |
| CO Conversion (@20 Hrs.) | 67 | 79 | 54 | 67 |
| Selectivity, mol. % | | | | |
| CH$_4$ | 9.7 | 11.5 | 9.9 | 11.7 |
| CO$_2$ | 0.2 | 0.7 | — | 0.3 |
| C$_2+$ | 90.1 | 87.8 | 90.1 | 88.0 |
| O$_2$ Chemisorption, μmol O$_2$/g catalyst | 213 | 265 | 178 | 202 |

The catalysts having the higher rutile content, or catalysts having the better cobalt metal dispersion (as measured by conventional dynamic O$_2$ chemisorption), are significantly more active in converting the CO and H$_2$ to hydrocarbons; albeit it will be noted, the gas and CO$_2$ content of the catalysts having the higher rutile content are slightly debited, and the C$_2+$ hydrocarbon content of the product slightly lower.

Example 9

In another series of demonstrations, cobalt was dispersed on portions of 60-150 mesh (Tyler) titania by the heat decomposition of a cobalt carbonyl compound, CO$_2$(CO)$_8$; deposited from a pentane solution; a procedure described by reference to articles by A. S. Lisitsyn, V. L. Kuznetsov, and Yu. I. Ermakov entitled (1) "Catalysts Obtained By The Reaction of Transition-Element Organometallic Compounds With Oxide-Sypport Surfaces, Hydrogenation of Carbon Monoxide on Catalysts Supports" and (2) "Catalysts Obtained By The Reaction Of Transition Element Organometallic Compounds With Oxygen-Support Surfaces. Catalytic Properties of Systems Prepared By The Pyrolysis of Co(CO)$_8$ on Oxide Supports In The Reaction CO+H$_2$ Depending On Their Composition And Pretreatment" Institute of Catalysis, Siberian Branch of the Academy of Sciences of the USSR, Novosibirsk. Translated from Kinetika i Kataliz, Vol. 23, No. 4, pp 919-931, July-August, 1982. Two of these catalysts, referred to in columns two and three in Table III, were prepared from TiO$_2$ having a rutile:anatase ratio of 1:2.6 (110 m$^2$/gm surface area), and are believed representative of prior art catalysts, and three of these catalysts referred to in columns four, five, and six were prepared from TiO$_2$ containing a rutile:anatase ratio >30:1. A sixth catalyst was prepared from cobalt nitrate, by impregnation of a TiO$_2$ support material having a rutile:anatase ratio >30:with a cobalt nitrate in acetone solution. The several catalysts, each of which contained between 9.3 wt. % and 11.1 wt. % cobalt as shown by analysis, were pretreated (1) at temperatures approximating 250° C. for one hour in vacuum, or (2) in air at this temperature for three hours followed by a one hour period of treatment at 450° C. with hydrogen, or (3) with hydrogen at 450° C. for one hour, as shown in the Table. Reference is made to Table IX.

TABLE IX 60-150 Mesh Catalysts, 200° C., 280 psig, GHSV = 1000, H$_2$/CO = 2.15

| Wt. % Co | 9.3 | 10.1 | 8.7 | 9.2 | 9.6 | 11.1 |

TABLE IX-continued

| 60-150 Mesh Catalysts, 200° C., 280 psig, GHSV = 1000, H$_2$/CO = 2.15 | | | | | | |
|---|---|---|---|---|---|---|
| Co Compound | Carbonyl | Carbonyl | Carbonyl | Carbonyl | Carbonyl | Nitrate |
| Rutile:Anatase Ratio of TiO$_2$ | 1:2.6 | 1:2.6 | >30:1 | >30:1 | >30:1 | >30:1 |
| Pretreatment | 257° C. - 1 hr in vacuo | Air 250° - 3 hr H$_2$ 450° - 1 hr | 257° C. - 1 hr in vacuo | Air 250° - 3 hr H$_2$ 450° - 1 hr | H$_2$ 450° - 1 hr | Air 250° - 3 hr H$_2$ 450° - 1 hr |
| % CO Conversion | 30 | 5 | 59 | 97 | 93 | 95 |
| Mol % CH$_4$ Selectivity | 13.5 | 15.1 | 4.9 | 5.4 | 5.6 | 4.5 |
| O$_2$ Chemisorption, μ mol O$_2$/g catalyst | — | 53 | — | 205 | 127 | 193 |

These data clearly show that the amount of conversion of the feed to hydrocarbons is very, very low with the catalysts prepared from a TiO$_2$ base containing a rutile: anatase ratio of 1:2.6 viz., 30 percent when the catalyst is treated at 257° C. for 1 hour under vacuum as described by the reference procedure, supra. It is even poorer, viz., 5 percent, when the catalyst is pretreated with air and then reduced in accordance with the process of this invention. Methane make is very, very high in either instance, viz., 13.5 percent and 15.1 percent, respectively. The superior performance of the catalyst formed from the high rutile: anatase TiO$_2$ support is particularly manifest when the % CO conversion between the catalysts formed from the low rutile: anatase TiO$_2$ support (30% and 5%, respectively) is compared with the % CO conversions obtained with the catalyst formed from the high rutile:anatase TiO$_2$ supports (59%, 97%, 93% and 95%, respectively). The CO conversion is poor because the poor dispersion of the cobalt, as determined by the O$_2$-chemisorption data.

In pretreating a catalyst of this invention, wherein the cobalt of the starting cobalt carbonyl compound is dispersed on a TiO$_2$ base having a rutile:anatase ratio of >30:1, the performance of the catalyst is drastically improved. Pretreating in accordance with the reference procedure, the percent CO conversion to hydrocarbons is essentially doubled, viz., 59 percent vis-a-vis 30 percent, and methane make is drastically reduced, viz., from 13.5 percent to 4.9 percent. When the preferred pretreat of the present invention is employed, i.e., air activation followed by hydrogen reduction, the percent CO conversion rises to 97 percent, with only 5.4 percent methane production; and even when a similar catalyst is reduced without a preceeding air treat, 93 percent CO conversion is obtained, with only 5.6 percent gas make.

The Co impregnated catalyst produced from a TiO$_2$ basehaving a rutile:anatase rateio >30:1, pretreated with both air and hydrogen, provides 95 percent selectivity of the CO to hydrocarbons, with a gas make of only 4.5 percent.

These reactions can be conducted with these catalysts in fixed bed, or slurry bed reactors with or without the recycle of any unconverted gas and/or liquid product. The C$_{10}$+ product that is obtained is an admixture of linear paraffins and olefins which can be further refined and upgraded to high quality middle distillate fuels, or such other products as mogas, diesel fuel, jet fuel, lubes specialty solvents and the like. A premium grade middle distillate fuel of carbon number ranging from about C$_{10}$ to about C$_{20}$ can also be produced from the C$_{10}$+ hydrocarbon product. The catalyst is constituted of cobalt or cobalt and thoria supported on a rutile form of TiO$_2$ or rutile-titania-containing support which can contain such non-acidic materials as SiO$_2$, MgO, ZrO$_2$, Al$_2$O$_3$. The catalyst is preferably reduced with a H$_2$-containing gas at start-up.

It is apparent that various modifications and changes can be made without departing the spirit and scope of the present invention.

What is claimed is:

1. A catalyst composition useful for the conversion of methanol or synthesis gas to hydrocarbons which consists essentially of cobalt, or cobalt and thoria in catalytically active amount composited with titania or a titania-containing support, wherein the titania support is one having a rutile:anatase ratio of at least about 2:3.

2. The composition of claim 1 wherein the catalyst consists essentially of cobalt dispersed on the support, the catalyst containing from about 2 percent to about 25 percent cobalt, based on the weight of the catalyst composition.

3. The composition of claim 2 wherein the catalyst contains from about 5 to about 15 percent cobalt, based on the weight of the catalyst composition.

4. The composition of claim 1 wherein the catalyst consists essentially of cobalt and thoria dispersed on the support, the catalyst containing from about 2 percent to about 25 percent cobalt, and from about 0.1 percent to about 10 percent thoria, based on the total weight of the catalyst.

5. The composition of claim 4 wherein the catalyst consists from about 5 percent to about 15 percent cobalt, and from about 0.5 percent to about 5 percent thoria.

6. The composition of claim 1 wherein the titania support is one having a rutile:anatase ratio of at least about 3:2.

7. The composition of claim 1 wherein the titania support is one having a rutile:anatase ratio ranging from about 3:2 to about 100:1, or greater.

8. The composition of claim 7 wherein the rutile:anatase of the support ranges from about 4:1 to about 100:1, and greater.

9. The composition of claim 1 wherein the titania promoted cobalt catalyst contains Co and ThO$_2$ in ratio of Co:ThO$_2$ ranging from about 20:1 to about 1:1.

10. The composition of claim 1 wherein the titania promoted cobalt catalyst contains Co and ThO$_2$ in ratio of Co:ThO$_2$ ranging from about 15:1 to about 2:1.

11. A catalyst composition particularly useful for the conversion of methanol to hydrocarbons which consists essentially of cobalt in catalytically active amount composited with titania or a titania-containing support, wherein the support is one having a rutile:anatase ratio ranging from about 2:3 to about 3:2.

12. The composition of claim 1 wherein the catalyst consists essentially of cobalt dispersed on a titania or a titania-containing support, the catalyst containing from about 5 percent to about 15 percent cobalt, based on the weight of the catalyst composition, and the titania support is one having a rutile:anatase ratio of at least about 3:2.

13. The composition of claim 12 wherein the rutile:anatase ratio of the support ranges from about 3:2 to about 100:1, or greater.

14. The composition of claim 12 wherein the catalyst contains both cobalt and thoria dispersed on the support, the catalyst containing from about 0.1 percent to about 10 percent thoria, based on the total weight of the catalyst.

15. The composition of claim 14 wherein the catalyst contains from about 0.5 percent to about 5 percent thoria.

16. The composition of claim 12 wherein the catalyst contains both cobalt and thoria dispersed on the support, the Co and $ThO_2$ being provided in ratio of Co:$ThO_2$ ranging from about 20:1 to about 1:1.

17. The composition of claim 16 wherein the titania promoted cobalt catalyst contains Co and $ThO_2$ in ratio of Co:$ThO_2$ ranging from about 15:1 to about 2:1.

* * * * *